United States Patent

Jordan

Patent Number: 5,711,418
Date of Patent: Jan. 27, 1998

[54] PACKAGED ORTHODONTIC ARCHWIRE ASSEMBLY

[75] Inventor: Russell A. Jordan, Rancho Cucamonga, Calif.

[73] Assignee: Minnesota Mining and Manufacturing Co., St. Paul, Minn.

[21] Appl. No.: 626,201

[22] Filed: Mar. 29, 1996

Related U.S. Application Data

[60] Provisional application No. 60/001,039, Jun. 28, 1995.

[51] Int. Cl.$^6$ .................................................. A61B 19/02
[52] U.S. Cl. ...................... 206/63.5; 206/499; 22/87.05
[58] Field of Search ........................... 206/570, 368, 206/369, 63.5, 438, 443, 499, 775, 776, 778; 229/87.05, 87.06

[56] References Cited

U.S. PATENT DOCUMENTS

| | | |
|---|---|---|
| 2,931,493 | 4/1960 | Pfohl . |
| 2,931,494 | 4/1960 | Pfohl . |
| 2,965,225 | 12/1960 | Zoller et al. . |
| 2,993,589 | 7/1961 | Zoller et al. . |
| 3,111,220 | 11/1963 | Bostrom . |
| 3,144,343 | 8/1964 | Fritsche . |
| 3,186,628 | 6/1965 | Rohde . |
| 3,246,747 | 4/1966 | Blish . |
| 3,255,869 | 6/1966 | Keller . |
| 3,315,802 | 4/1967 | Lonholdt et al. . |
| 3,429,432 | 2/1969 | Cabernoch et al. . |
| 3,547,257 | 12/1970 | Armentrout . |
| 3,625,351 | 12/1971 | Eisenberg . |
| 4,055,672 | 10/1977 | Hirsch et al. . |
| 4,108,309 | 8/1978 | Bronner . |
| 4,116,338 | 9/1978 | Weichselbaum . |
| 4,251,712 | 2/1981 | Parr . |
| 4,355,721 | 10/1982 | Knott, II et al. . |
| 4,537,305 | 8/1985 | Takanashi . |
| 4,848,066 | 7/1989 | Luhman . |
| 4,881,644 | 11/1989 | Norquest et al. . |
| 4,900,251 | 2/1990 | Andreasen . |
| 4,917,929 | 4/1990 | Heinecke . |
| 4,977,003 | 12/1990 | Brown et al. . |
| 4,979,611 | 12/1990 | Bolliger et al. . |
| 5,221,202 | 6/1993 | James ................... 206/63.5 X |
| 5,328,363 | 7/1994 | Chester et al. . |
| 5,346,061 | 9/1994 | Newman et al. ............ 206/63.5 X |
| 5,348,154 | 9/1994 | Jacobs et al. . |

FOREIGN PATENT DOCUMENTS

| | | |
|---|---|---|
| 0 609 653 A1 | 10/1994 | European Pat. Off. . |
| 37333524 A | 3/1987 | Germany . |

*Primary Examiner*—Jacob K Ackun
*Attorney, Agent, or Firm*—Gary L. Griswold; Walter N. Kirn; James D. Christoff

[57] ABSTRACT

Orthodontic archwires are packaged between pairs of flexible sheets that are releasably fixed to each other. The archwires are spaced apart from each other between the sheets and arranged in a nested array wherein a portion of one archwire is received within the U-shaped configuration of another archwire. Lines of weakness extend between adjacent pairs of the archwires for enabling detachment of one archwire from remaining archwires of the assembly when desired.

9 Claims, 4 Drawing Sheets

PACKAGED ORTHODONTIC ARCHWIRE ASSEMBLY

CROSS-REFERENCE TO RELATED APPLICATION

This application claims priority to Provisional U.S. patent application Ser. No. 60/001,039 filed Jun. 28, 1995.

BACKGROUND OF THE INVENTION

1. Field of the Invention

This invention relates to an assembly of an orthodontic archwire and a package initially covering and protecting the archwire.

2. Description of the Related Art

Orthodontic treatment often involves the use of a variety of small articles. For example, orthodontic treatment typically includes the use of small, slotted appliances known as brackets that are fixed to the teeth of the patient's upper and lower dental arch. An archwire is placed in the slot of each bracket, and serves as a track to guide movement of the teeth to orthodontically correct positions. In addition, appliances known as buccal tubes are often fixed to the molar teeth and serve as an anchor for ends of the archwire.

A variety of different archwires are available, and it is common practice for an orthodontist to retain a number of different archwires on hand for use when needed. Archwires are available in varying overall sizes to match the size of the patient's upper or lower dental arch. In addition, archwires may have a round, square or rectangular cross-sectional configuration and may be of different cross-sectional sizes in accordance with the orthodontist's preferred treatment technique.

Often, only a single set of brackets is affixed to the patient's teeth during the course of treatment. However, the archwire may be changed at selected intervals in the treatment program and replaced with another archwire having somewhat different characteristics. For example, an archwire having a relatively low stiffness may be used initially when the teeth are located some distance from their intended final position so that undue and possible painful forces are not experienced by the patient. As the teeth move closer to their desired final positions, the archwire can be replaced with an archwire having a higher stiffness in order to facilitate moving the teeth over the remaining distances.

Orthodontic archwires are also available in a number of different materials and constructions. As examples, archwires are commonly available in a number of different alloys, including alloys of stainless steel, alloys of nitinol (which principally comprise nickel and titanium, but which may also include small amounts of other components such as copper or cobalt) and cobalt-based nickel alloys. The archwires may have a square, rectangular or circular configuration in transverse cross-section. Moreover, the archwires may be made of a solid, unitary section of wire or may be made of a number of multiple strands that are braided, twisted or wrapped around a core in coaxial fashion.

A number of packaging systems have been used in the past to store and dispense orthodontic archwires. In some instances, a number of identical archwires are packaged in a single carton. Unfortunately, such packaging may provide an opportunity for remaining archwires in the carton to be contaminated whenever the carton is opened to remove a single archwire.

There has also been increased interest in recent years in unit-of-use packaging, wherein a single archwire is packaged in its own container and consequently is less likely to be cross-contaminated. In some instances, the archwire and the interior of the container have been sterilized by the manufacturer. Other containers are not sterilized by the manufacturer, but are adapted to be placed in an autoclave by the orthodontist to sterilize the container and its contents.

Many orthodontic archwires have been packaged in pouches. Some pouches are reduced-sized versions of well-known plastic sandwich bags that have a zipper-type closure on one end. Such pouches sometimes have a printed label adhered by a pressure sensitive adhesive to its outer surface. Moreover, some pouches have a printed insert that is placed inside the pouch next to the appliance.

Other pouches for orthodontic archwires are made by cutting two panels or sheets into a square or rectangular configuration of equal size, and then adhering or otherwise joining the sheets together along their periphery to enclose an archwire between the sheets. One sheet is made of a flexible clear plastic material to facilitate viewing of the packaged archwire. The other sheet is often made of a flexible paper or other material having a printable surface, so that the manufacturer's name, a description of the packaged archwire and other information such as instructions, notices or lot numbers may be provided directly on the pouch.

There is a continuing need in the art to improve packaging for orthodontic devices, including orthodontic archwires. In particular, there is a need for an improved unit-of-use package which uses less packaging materials than conventional packages. Preferably, such an improved package will facilitate shipping, storage and dispensing of the archwires so that a number of packaged archwires can be handled simultaneously without undue effort and without requiring substantial space. Moreover, there is a need to improve conventional methods of displaying stored orthodontic archwires, so that the proper archwire can be easily stored and yet readily selected by the orthodontist when needed.

SUMMARY OF THE INVENTION

The present invention concerns a packaged orthodontic archwire assembly that comprises a first sheet and a second sheet extending over and releasably fixed to the first sheet. A plurality of orthodontic archwires are received between the first sheet and the second sheet. Each of the archwires has a generally U-shaped configuration and has a pair of spaced apart leg portions and a bight portion integrally interconnecting the leg portions. The archwires are spaced apart from each other and arranged in a nested array wherein a portion of one archwire is received within the U-shaped configuration of another archwire. At least one of the sheets includes one or more lines of weakness extending between adjacent pairs of the archwires for enabling detachment of one archwire from remaining archwires of the assembly when desired.

The nested array of archwires substantially reduces the space that might otherwise be required for shipping, storage and dispensing of the archwires. Yet, each archwire is individually packaged between sections of the sheet so that the likelihood of cross-contamination is significantly reduced. The assembly is particularly suited for manufacture in automated fashion.

DETAILED DESCRIPTION OF THE PREFERRED EMBODIMENTS

Figure 1:
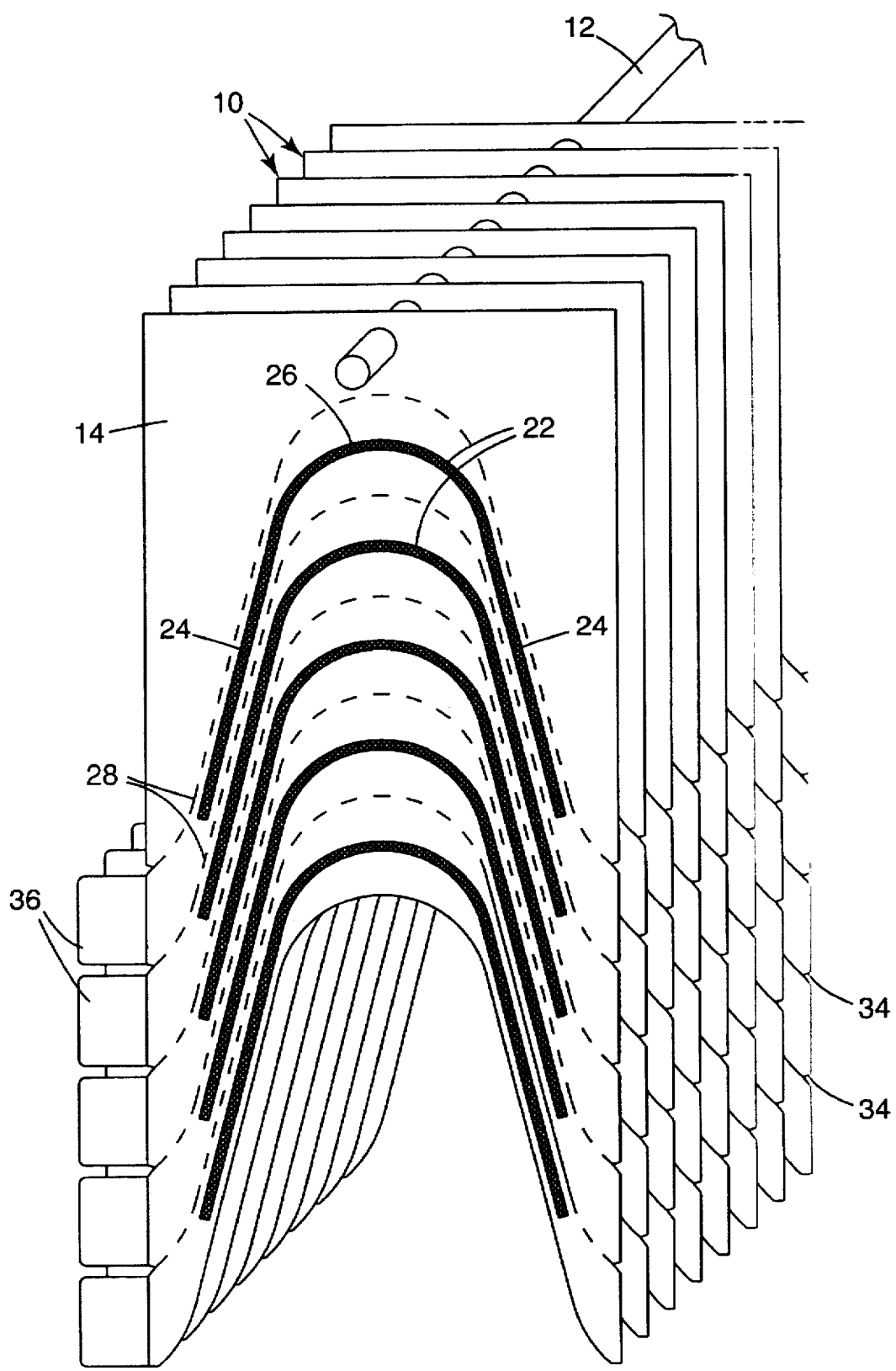
FIG. 1 is a perspective view showing a number of assemblies according to the invention as they appear when hanging from a dispensing peg.

A packaged orthodontic archwire assembly is designated by the numeral 10 in FIGS. 1–4. Each assembly includes an upper section with a hole, and in FIG. 1 a number of the assemblies 10 are received on a dispensing peg 12 for storage and dispensing.

Each assembly 10 includes a first sheet 14 and a second sheet 16 that extends over the first sheet 14. An exaggerated cross-section of the sheets 14, 16 is shown in FIGS. 3 and 4.

The first sheet 14 is preferably made of flexible material, and most preferably is a clear transparent plastic material such as polyethylene. The second sheet 16 is also preferably made of flexible material, and is most preferably made of a material having at least one printable surface. A suitable material for the second sheet 16 is paper.

Figure 3:
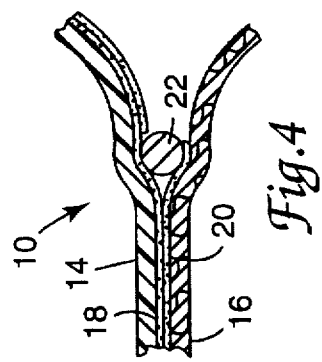
FIG. 3 is an enlarged, fragmentary, cross-sectional view of a portion of one of the sections shown in FIG. 2, wherein the scale has been exaggerated for purposes of explanation.
Figure 4:
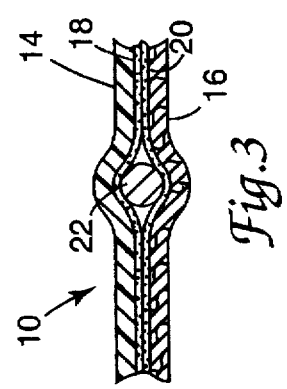
FIG. 4 is a view somewhat similar to FIG. 3 except that sheets of the section have been pulled apart in order to gain access to an archwire.

As illustrated in FIG. 3, a layer of cohesive 18 is in contact with the first sheet 14, and a layer of cohesive 20 is in contact with the second sheet 16. The layers of cohesive 18, 20 adhere to themselves and also to their respective underlying sheets 14, 16, but do not strongly adhere to other materials such as orthodontic archwires. Suitable cohesive materials include latex-based materials.

A suitable plastic sheet and cohesive assembly for the sheet 14 and the cohesive 18 is known as cold-seal sterile packaging, anchor web (cling free film); no. RC4101 from Phoenix Health Care Products. A suitable paper sheet and cohesive assembly for the sheet 16 and the cohesive 20 is known as cold-seal sterile packaging, transfer web (35–40 lb/ream paper); no. D1102 from Phoenix Health Care Products.

Figure 2:
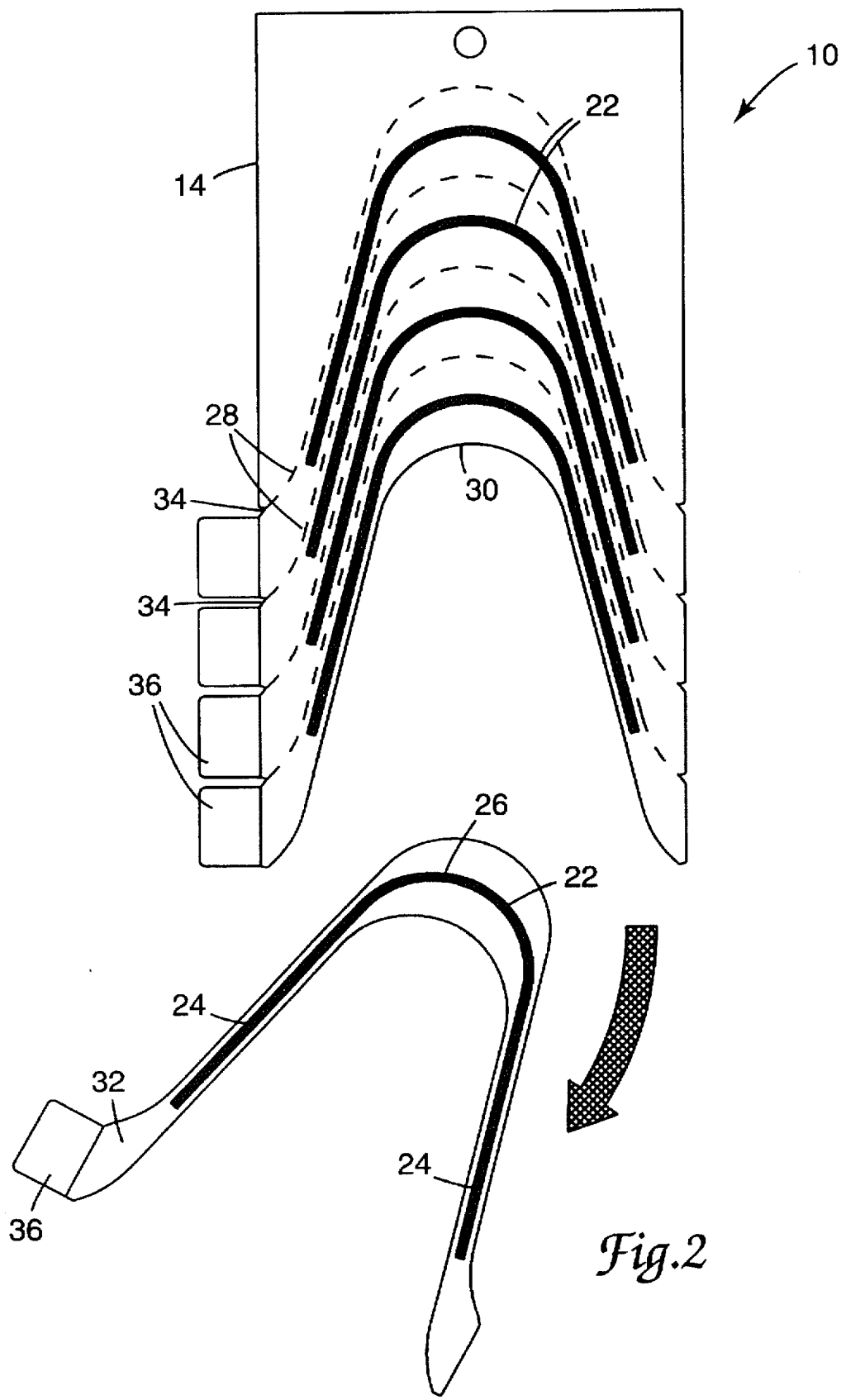
FIG. 2 is a front elevational view of one of the assemblies shown in FIG. 1, except that a lower section of the assembly has been detached from remaining sections of the assembly.

As shown in FIGS. 1 and 2, a plurality of orthodontic archwires 22 are received between the first sheet 14 end the second sheet 16. Each of the archwires 22 has a pair of spaced apart leg portions 24 and a bight portion 26 integrally interconnecting the leg portions 24. The archwires 22 have a concave or generally U-shaped configuration. The leg portions 24 may be parallel to each other, or diverge at an acute angle away from each other as the free ends of the leg portions 24 are approached.

The archwires 22 are spaced apart an equal distance from adjacent archwires, and are arranged in a nested array. In the array shown in FIGS. 1 and 2, each archwire 22 is oriented in essentially the same direction and is parallel to the remaining archwires 22 of the assembly 10.

The archwires 22 may have any one of a number of cross-sectional configurations such as round, rectangular or square. The archwires 22 may be made of various alloys of stainless steel, nickel-titanium or other materials such as are known in the art and may be solid or made from a number of twisted or braided filaments. Suitable archwires are sold under the brands names NITINOL XL, NITINOL SE and HI-T, from 3M Unitek.

A line of weakness 28 extends in the sheets 14, 16 between each adjacent pair or archwires 22 as shown in FIGS. 1 and 2 and has a concave or generally U-shaped configuration somewhat similar to the configuration of the archwires 22. The lines of weakness 28 are made of a series of spaced apart perforations or are made by cutting or indenting one or both of the sheets 14, 16 to a controlled depth. The lines of weakness 28 define separate sections surrounding each archwire 22 of the assembly 10, and each section includes a portion of the first and second sheet 14, 16. Examples of the sections are designated by the numerals 30 and 32 in FIG. 2.

The sections of the assembly 10 can be pulled apart from each other when it is desired to dispense and use an archwire 22. For example, the section 32 as shown in FIG. 2 has been detached from the section 30 as well as the remaining sections of the assembly 10. The sheets 14, 16 preferably include notches 34 located at both ends of each line of weakness 28 in order to facilitate rupturing the assembly 10 along the selected line of weakness 28 when desired.

Preferably, each of the sheets 14, 16 includes a series of side pull tabs 36 that are each associated with a single, corresponding section. The cohesive associated with the pull tabs 36 is masked to facilitate grasping and separation of the pull tabs 36. Alternatively, the pull tabs 36 lack a layer of cohesive to facilitate grasping and separation. Once the pair of pull tabs 36 of one section of the assembly 10 have been grasped by separate hands, the pull tabs 36 are pulled away from each other to release the first sheet 14 from the second sheet 16.

Typically, the chosen section will be detached from remaining sections along the corresponding line of weakness 28 before the pull tabs 36 are used to open that section. As an option, the pull tab 36 of the first sheet may be of a different length in a horizontal direction viewing FIGS. 1 and 2 than the pull tab of the second sheet 16 in order to facilitate grasping of the sheets 14, 16 by separate hands.

As the pull tabs 36 are lifted apart from each other, one of the layers of cohesive 18, 20 lifts from its adjacent, respective sheet 14, 16 and instead adheres to the other layer of cohesive 18, 20 as shown in FIG. 4. After the sheets 14, 16 are substantially separated from each other, the archwire 22 can be readily grasped by a tool or by hand, and then separated from any remaining portion of the sheets 14, 16 and used as desired. Advantageously, after one of the layers of cohesive 18, 20 detaches from its original, adjacent sheet 14, 16, such layer will generally not re-adhere to such sheet and thereby provide a tamper evident indication that the section has been opened.

Figure 5:
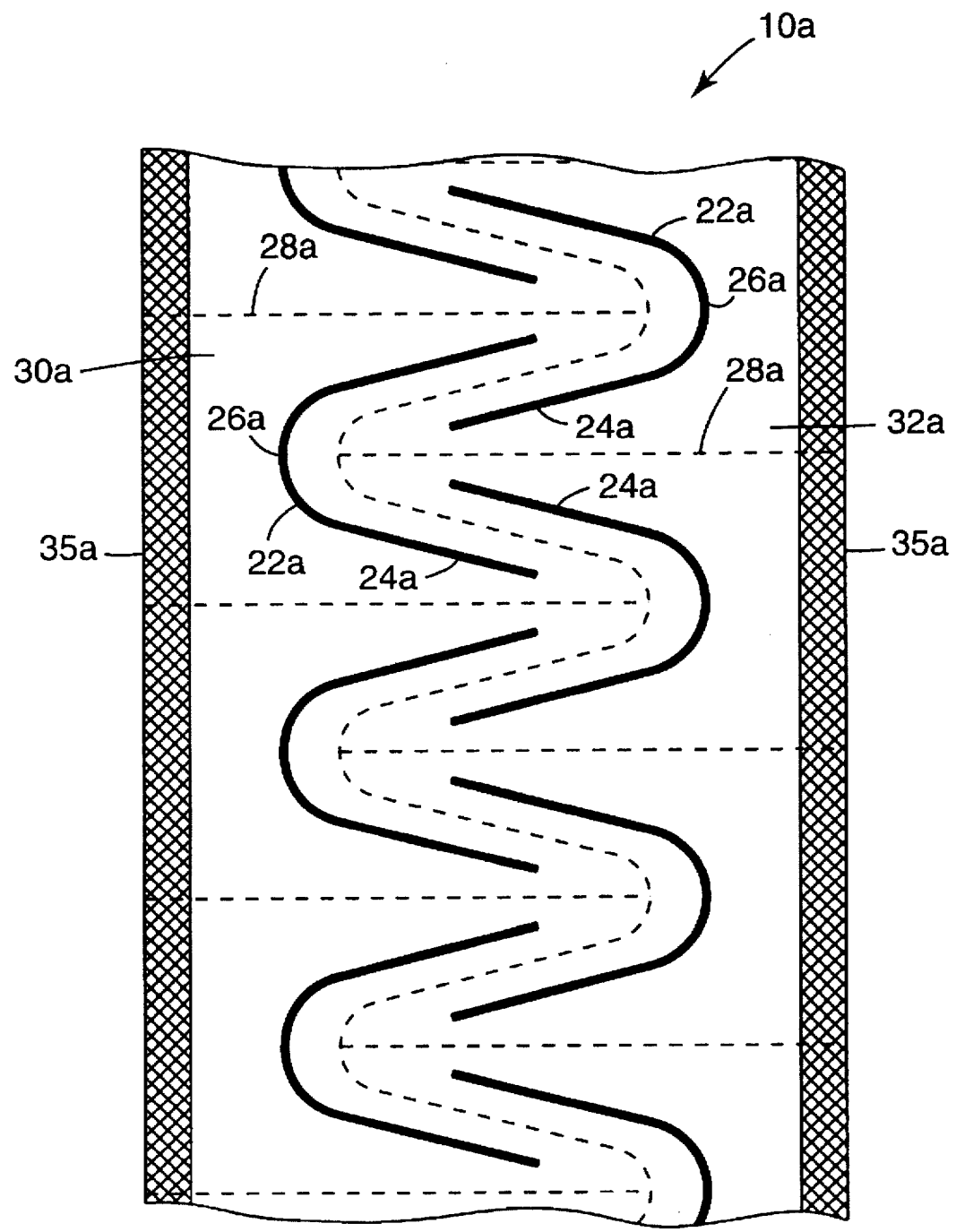
FIG. 5 is a fragmentary, front elevational view of a packaged archwire assembly according to another embodiment of the invention.

The embodiment of the invention that is illustrated in FIG. 5 concerns an assembly 10a that is similar in many respects to the assembly 10 shown in FIGS. 1–4. The assembly 10a includes a first sheet, a second sheet extending over the first sheet and a series of archwires 22a received between the first sheet and the second sheet. The first sheet and the second sheet are made of the same materials described in connection with the first sheet 14 and the second sheet 16 described above. In addition, the first sheet and the second sheet are each coated with a layer of cohesive that is similar to the layers of cohesive 18, 20 described above.

Likewise, the archwires 22a are similar in shape and materials of construction to the archwires 22 described above. However, the archwires 22a are arranged in a somewhat different nested array. In FIG. 5, the leg portions 24a of each archwire 22a extend into the concavity and toward the bight portion 26a of the next adjacent archwire. As such, two leg portions 24a of different archwires 22a are received within the U-shaped configuration of a third archwire 22a.

The assembly 10a also includes lines of weakness 28a that are similar in construction to the lines of weakness 28 described above. However, the lines of weakness 28a have a somewhat different configuration to match the nested array of archwires 22a. The lines of weakness 28a, like the lines of weakness 28, enable sections of the assembly 10a (such as section 30a) to be detached from the next adjacent section (such as section 32a) when desired.

The assembly 10a optionally includes notches (not shown) similar to notches 34 to facilitate rupture along the lines of weakness 28a. Further, outer edge portions 35a along each side of the assembly 10a lack cohesive and thereby function as easy-to-grasp pull tabs similar to the pull tabs 36.

Figure 6:
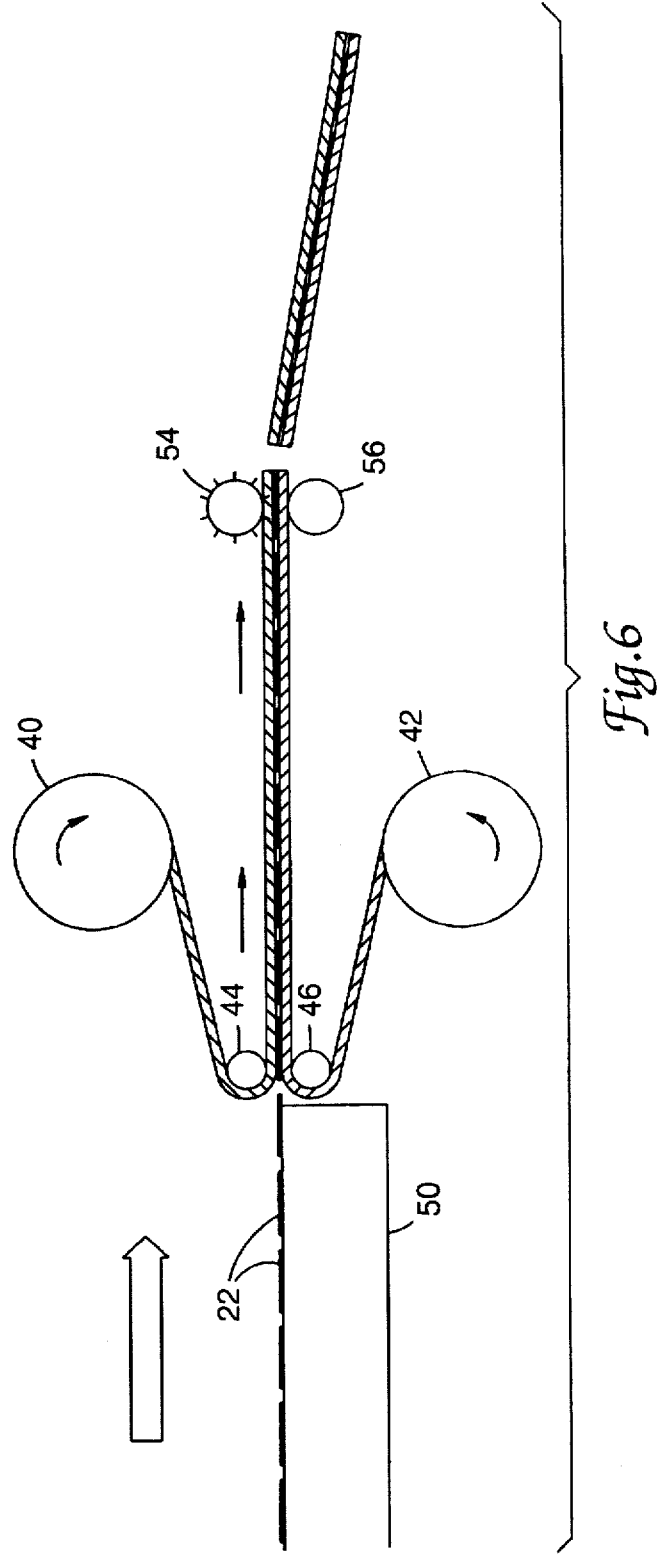
FIG. 6 is a reduced elevational view in schematic form of a method of manufacturing the assemblies shown in FIGS. 1 and 2.

A method of manufacturing the packaged orthodontic archwire assembly according to the invention is depicted in FIG. 6. The method includes the use of a roll 40 of a clear plastic web (such as polyethylene) that is coated with a cohesive and a roll 42 of a paper web that is coated with cohesive. The plastic and paper webs advance around respective pressure rollers 44, 46 in such a manner that the cohesive layer of one web contacts the cohesive layer of the other web as the webs meet at the nip between the rollers 44, 46.

A transport table 50 includes a conveyor for moving a series of spaced apart, individual archwires 22 toward the nip between the pressure rollers 44, 46 as the webs continue to advance. The archwires 22 are thereby inserted between the webs. The assembly of the webs and the archwire then advance to a perforation roller 54 that provides lines of weakness such as lines of weakness 28 or 28a in one or more of the webs. As an alternative, the perforation roller 54 can instead be a controlled depth cut rotary die that provides the lines of weakness. An anvil 56 roller is located directly beneath the roller 54 to provide support for the perforation or cutting operation.

At appropriate intervals of time, advancement of the archwires 22 along the transport table 50 is interrupted so that certain adjacent pairs of archwires are not nested with each other but instead are spaced relatively far apart from each other. When such certain pairs move past the perforation roller 54, a cutting knife (not shown) severs the webs in the relatively large space between such certain pairs to provide a completed packaged archwire assembly similar to that shown in FIGS. 1, 2 or 5 that is ready for stock or shipment.

A variety of methods are available for printing identifying text on the packaged archwire sections such as the manufacturer's name, the identity of the archwire by size, material, shape or other characteristics, cautionary notices and lot numbers. The printed information can be pre-printed on the paper web. Alternatively, a printer can be located next to the paper web as it advances. Another alternative involves the use of a labeler which prints and attaches a pressure sensitive adhesive label to one or more sides of the completed archwire assembly as the assembly advances.

I claim:

1. A packaged orthodontic archwire assembly comprising:

a first sheet;

a second sheet extending over and releasably fixed to said first sheet; and a plurality of orthodontic archwires received between said first sheet and said second sheet, each of said archwires having a generally U-shaped configuration and having a pair of spaced apart leg portions and a bight portion integrally interconnecting said leg portions, said archwires being spaced apart from each other and arranged in a nested array wherein a portion of one of said archwires is received within the U-shaped configuration of another of said archwires, and wherein at least one of said sheets includes one or more lines of weakness extending between adjacent pairs of said archwires for enabling detachment of one archwire from remaining archwires of said assembly when desired.

2. The packaged orthodontic archwire assembly of claim 1, wherein said nested array includes an arrangement wherein each of said archwires is generally parallel to the remaining archwires.

3. The packaged orthodontic archwire assembly of claim 1, wherein said nested array includes an arrangement wherein leg portions of two of said archwires extend toward a bight portion of a third archwire disposed between said two archwires.

4. The packaged orthodontic archwire assembly of claim 1, including a cohesive for releasably fixing said first sheet to said second sheet.

5. The packaged orthodontic archwire assembly of claim 1, wherein said first sheet is made of a transparent plastic material.

6. The packaged orthodontic archwire assembly of claim 1, wherein said second sheet is made of a flexible material having a printable surface.

7. The packaged orthodontic archwire assembly of claim 1, including pull tabs connected to said first sheet and said second sheet, said pull tabs being not directly joined to each other for facilitating separation of said first sheet from said second sheet.

8. The packaged orthodontic archwire assembly of claim 1, wherein said lines of weakness include a series of spaced apart perforations.

9. The packaged orthodontic archwire assembly of claim 1, wherein said lines of weakness include a generally continuous controlled depth cut.

* * * * *